(12) United States Patent
Su et al.

(10) Patent No.: US 6,844,024 B2
(45) Date of Patent: Jan. 18, 2005

(54) METHODS FOR COATING IMPLANTS

(75) Inventors: Shih-Horng Su, Westford, MA (US); Tung-Liang Lin, Acton, MA (US)

(73) Assignee: AST Products, Inc., Billerica, MA (US)

( * ) Notice: Subject to any disclaimer, the term of this patent is extended or adjusted under 35 U.S.C. 154(b) by 0 days.

(21) Appl. No.: 10/462,122

(22) Filed: Jun. 13, 2003

(65) Prior Publication Data

US 2004/0253366 A1 Dec. 16, 2004

(51) Int. Cl.$^7$ .................................................. B05D 3/00
(52) U.S. Cl. .................... 427/2.24; 427/2.25; 427/2.28; 427/359; 427/232; 427/235
(58) Field of Search .............................. 427/2.1, 2.24, 427/2.25, 2.28, 2.3, 355, 359, 235, 232

(56) References Cited

U.S. PATENT DOCUMENTS

| | | | |
|---|---|---|---|
| 5,534,287 A | * 7/1996 | Lukic | 427/2.25 |
| 6,153,252 A | 11/2000 | Hossainy et al. | 427/2.3 |
| 6,187,370 B1 | * 2/2001 | Dinh et al. | 427/2.24 |
| 6,517,889 B1 | * 2/2003 | Jayaraman | 427/2.24 |
| 2003/0077312 A1 | * 4/2003 | Schmulewicz et al. | 424/426 |

* cited by examiner

Primary Examiner—Bret Chen
(74) Attorney, Agent, or Firm—Fish & Richardson P.C.

(57) ABSTRACT

A method of coating a polymer onto an implant having at least one interstice. The method includes (1) providing a solution containing a polymer; (2) applying the solution onto the implant; (3) and removing the solution spanning the interstice by (a) contacting the outer surface of the implant with a surface of a substrate, so that the solution spanning the interstice is drawn to the surface of the substrate via affinity between them; or by (b) bursting and removing the solution spanning the interstice on the implant with an air pressure difference before drying; and (4) drying the solution to form a coating.

15 Claims, No Drawings

METHODS FOR COATING IMPLANTS

BACKGROUND

Implants have been used for reconstructing damaged tissues and restoring their functions. For example, an expandable metal stent is commonly used in transluminal procedures, such as angioplasty, to restore adequate blood flow. However, a stent may stimulate host responses, resulting in thrombosis and restenosis. To avoid these complications, it is often coated with an anti-arteriosclerosis or anti-restenosis agent before being deployed in a blood vessel.

An expandable metal stent has dimensionally manipulatable interstices on its wall. Conventional methods for coating such a stent often lead to bridges, i.e., films spanning interstices. Bridges interfere with the expansion of the stent during its deployment. Also, they may rupture upon expansion and thereby activate platelet deposition due to flow disturbances in a hemodynamic environment. Further, pieces of bridges may fall off and cause downstream emboli. Finally, bridges may prevent endothelial cells from migrating into the stent and encapsulating it.

There is a need for a method of preparing bridge-free coating on a stent, as well as other implants having interstices.

SUMMARY

The present invention relates to a novel method of forming a bridge-free polymeric coating on an implant having one or more interstices. The method is suitable for coating an implant having interstices that may otherwise be blocked with bridges if conventional coating methods are used.

The method of this invention requires the use of a solution containing a polymer. It includes applying the solution onto an implant that has interstices and, before drying, removing the solution spanning the interstices.

To remove a solution spanning the interstices of an implant, one can contact the outer surface of the implant with a surface of a substrate so that the solution is drawn to the surface of the substrate via affinity between the solution and the surface. Preferably, the implant is simply rolled over a flat or concaved surface of a substrate. The substrate can be made of glass, quartz, sponge saturated by the solution, ceramic, stainless steel, paper, leather, or polymeric material.

One can also remove a solution spanning the interstices by bursting and removing it via an air pressure difference. For example, when an implant is tubular, one can insert into the implant a tube so that a first opening of the tube is in close proximity to the inner surface of the implant, and a second opening of the tube adapted for connecting to an aspirating instrument. During operation of the aspirating instrument, an air pressure difference exists between the first opening and the inner surface of the implant. As a result, the solution spanning the interstices is burst due to the air pressure difference and removed via the tube. The implant can be moved along the tube to facilitate the bursting and removing of the solution spanning all interstices of the implant.

The above-described coating method can be used to coat a dimensionally manipulatable implant, such as a stent used in angioplasty or a coil used in embolization. The coating solution can contain a biodegradable polymer (e.g., polyglycolic acid) or a non-biodegradable polymer (e.g., polyurethane). In addition to a polymer, the coating solution can also contain a pharmaceutically active agent, such as an anti-inflammation drug (e.g., curcumin).

The details of one or more embodiments of the invention are set forth in the accompanying description below. Other advantages, features, and objects of the invention will be apparent from the detailed description and the claims.

DETAILED DESCRIPTION

The method of this invention can be used for coating a dimensionally manipulatable implant having interstices. The coating formed on the implant follows the exact contour of the implant. As such, its physical integrity is maintained when the implant is subjected to dimensional change. In contrast, conventional coating methods result in bridges that may restrict dimensional change of the implant, and break off upon the change.

For example, the method can be used to coat a polymer and a pharmaceutically active agent onto a stent, i.e., an expandable tubular implant used for restoring blood vessel function. A stent is generally cylindrical and perforated with interstices that are longitudinal, ovoid, circular, or of any other desired regular or irregular shapes. It may be composed of helically wound or serpentine wires with interstices between the wires. It can be made of biocompatible materials, such as metals, and nonmetallic materials, such as polymers. Suitable biocompatible metals include, but are not limited to, stainless steel, tantalum, titanium alloys, and cobalt alloys. Suitable nonmetallic biocompatible materials include biostable materials, such as polyamides, polyolefins (e.g., polypropylene and polyethylene), and polyethylene terephthalate; and bioabsorbable materials, such as collagen, homopolymers and copolymers of lactic acid, glycolic acid, lactide, glycolide, para-dioxanone, trimethylene carbonate, epsilon-caprolactone; and blends thereof. The method of the present invention can also be used for coating a polymer onto a dimensionally manipulatable coil and any other devices having one or more interstices.

To practice a method of this invention, one can first dissolves a polymer and a pharmaceutically active agent in a suitable solvent to form a coating solution. A solvent can be chosen based on evaporation rate of the solvent, viscosity of the polymer solution, deposition level of the polymer, solubility of the active agent, and wetting of the implant to be coated. In a preferred embodiment, the polymer and the active agent are both soluble in the solvent. In another embodiment, the coating polymer is soluble in the solvent and the active agent is dispersed in the polymer solution. In the latte case, the solvent must be able to suspend small particles of the active agent without causing them to form aggregates that may clog the interstices of the implant. Mixed solvent systems can also be used to control the viscosity and evaporation rate. In all cases, the solvent must not inactivate the active agent. Preferred solvents include but are not limited to water, acetone, N-methylpyrrolidone, dimethyl sulfoxide, toluene, methylene chloride, chloroform, 1,1,2-trichloroethane, various freons, dioxane, ethyl acetate, tetrahydrofuran, dimethylformamide, and dimethylacetamide. The polymer can be a biodegradable polymer or a non-biodegradable polymer. Examples of a biodegradable polymer include polyglycolic acid poly(L-lactic acid) (PLLA), poly-lactic/polyglycolic acid co-polymer, poly(epsilon caprolactone) (PCL), polyanhydrides, polyorthoesters, poly vinly acetate, polyhydroxybutyrate-polyhydroxyvalerate, aliphatic polyesters, and collagen. Examples of a non-biodegradable polymer include polyurethane, polyacrylates, polymethacrylates, polyethylene and polypropylene copolymers, epoxides, polyamides, polyesters, and parylene. Blend or block copolymers and combination of these polymers can also be used to practice the method. Further, one can use a polymer that is liquid at room temperature to practice the method. Such a liquid polymer can be used as a coating solution directly.

A coating solution can be coated on an implant by dipping, brushing, spraying, chemical vapor depositing, or a combination thereof. Then, before drying, one removes the excess solution spanning the interstices of the implant. To remove the excess solution, one can contact the outer surface of the implant with a surface of a substrate, so that the solution is drawn to the surface of the substrate via affinity between the solution and the surface. In one example, the excess solution is removed by rolling the implant over a substrate surface. The rolling enables the substrate surface to contact with all parts of the outer surface of the implant, thereby dragging excess solution spanning the interstices on the implant. To facilitate rolling, the surface of the substrate is preferably flat or concaved. The substrate can be made of glass, quartz, poly(vinyl pyrrolidone) (PVP) sponge, ceramic, stainless steel, paper, or leather. A suitable substrate can be chosen based on the following two criteria (1) the substrate is inert to the solvent used to dissolve the polymer, and (2) the affinity between the substrate and the solvent is strong enough to drag the solvent spanning interstices of an implant. Preferably, the solution drawn to the substrate surface evaporated rapidly so that, during the rolling, it does not reenter the interstices or dissolve the polymer coated on the implant. This method is therefore suitable for removing a coating solution having high volatility, e.g., a solution based on 1,4-dixoane, chloroform, acetone, methanol, ethanol, or hexane. Note that, the affinity between PVP sponge and 1,4-dixoane is stronger than that between glass and the solvent. Thus, one can use PVP sponge to remove a 1,4-dixoane-based coating solution from the interstices of an implant when glass cannot completely remove it.

One can also remove the solution spanning the interstices of an implant by bursting and removing it via an air pressure difference. When the implant is tubular, one can insert into the implant a tube, such as a glass pipette as described below in Example 2. The tube has a first opening, which, after the insertion, is in close proximity to the inner surface of the implant. The tube also has a second opening that is adapted for connecting to an aspirating instrument. To remove the solution spanning the interstices, one connects the second opening to an aspirating instrument. During operation of the aspirating instrument, an air pressure difference exists between the first opening and the inner surface of the implant. As a result, the solution spanning the interstices of the implant is burst by the air pressure difference and removed via the tube. In one example, during operation, the implant is moved along the tube so that the solution spanning all interstices of the implant can be burst and removed. This method is not suitable for removing a coating solution having high volatility, since the solution dries rapidly and forms bridges before being burst and removed. Instead, it is suitable for removing a coating solution having low volatility, such as a water, dimethylsulfoxide, or tetrahydrofuran-based solution.

After removing the solution spanning the interstices, the implant can be dried according to methods well known in the art, e.g., that described in U.S. Pat. No. 6,517,889, to form a bridge-free coating. When a liquid polymer is coated, it can be solidified using photocuring methods known in the art. See, e.g., U.S. Pat. No. 6,565,968.

To practice the method of this invention, one can include a pharmaceutically active agent in a coating solution and coat the agent onto an implant, such as a stent used in angioplasty. It is known that angioplasty often results in injury to the wall of a blood vessel. The injury induces smooth muscle cell proliferation (i.e., hyperplasia), which in turn leads to re-narrowing of the vessel (i.e., restenosis). The injury also triggers inflammation responses, which are closely related to later stage restenosis as well as thrombosis. To prevent restenosis and thrombosis, a stent can be coated with an anti-cell proliferation agent, an anti-inflammation agent, an immuno-suppressant, an anti-thrombosis agent, an anti-platelet agent, a fibrinolysis agent, or an extracellular matrix mediator. The stent, once implanted into a blood vessel, delivers any of these active agents to the blood vessel. Examples of these active agents are listed in Table 1 below.

TABLE 1

Exemplary Pharmaceutically Active Agents

| Category | Active Agent |
| --- | --- |
| Anti-inflammation agents | alclometasone, amcinonide, amlexanox, balsalazide, betamethasone, celecoxib, choline magnesium trisalicylate, choline salicylate, chlobetasol, colchicine, cortisone acetate, curcumin, disunite, dexamethasone, diclofenac, diflunisal, etodolac, fenoprofen, fluocinolone, fluometholone, flurandrenolide, flurandrenolide, flurbiprofen, hydrocortisone, ibuprofen, indomethacin, ketoprofen, ketorolac, meclofenamate, mefenamic acid, meloxicam, mesalamine, MethylPREDNISolone, nabumetone, naproxen, olsalazine, oxaprozin, piroxicam, PredniSONE, rofecoxib, salsalate, sulfasalazine, sulindac, tolmetin, triamcinolone, valdecoxiband, and their analogues and derivatives |
| Immuno-suppressant | azathioprine, basiliximab, cyclosporine, daclizumab, leflunomide, lymphocyte immune globulin, methotrexate, muromonab-CD3, mycophenolate, sirolimus, tacrolimus, thalidomideand, and their analogues and derivatives |
| Anti-cell proliferation agents | alkylating agents (busulfan, cisplatin, cyclophosphamide, oxaliplatin, etc.); alkylating agents, nitrosourea (carmustine, lomustine, etc.); anthracycline (epirubicin, mitoxantrone, etc.); antiandrogen (bicalutamide, flutamide, nilutamide, etc.); antibiotics (bleomycin, dactinomycin, mitomycin, etc.); antimetabolite (cladribine, flurouracil, gemcitabine, hydroxyurea, methotrexate, etc.); antimicrotubular (docetaxel, paclitaxel, etc.); aromatase inactivator (anastrozole, exemestane, etc.); hormone (estramumustine, megestrol); monoclonal antibody (alemtuzumab, rituximab, etc); protein synthesis inhibitors (asparaginase, pegaspargase); carboplatin, dipyridamole, doxorubin, doxorubicin, etoposide, imatinib, misonidazole, mercaptopurine, testolactone, trimetrexate glucuronate, tiripazamine, topotecan, vindesine, vincristine, and their analogues and derivatives |
| Anti-thrombosis, Anti-platelet, Fibrino-lysis agents, and Extra-cellular matrix mediator | abcimab, antithrombin III, argatroban, aspirin, clopidogrel, dipyridamole, eptifibatide, fondaparinux, heparin, low molecular weight heparin, recombinant hirudin (bivalirudin, lepirudin), ticlopidine, tissue recombinant plasminogen activators (alteplase, reteplase, streptokinase, tenecteplase, urokinase), tirofibanand, and their analogues and derivatives calprotectin, catechins, sulfonylated amino acid hydroxamates, tetracyclines (demeclocycline, doxycycline, minocycline, oxytetracycline, tetracycline), and their analogues and derivatives |

To effectively prevent restenosis and thrombosis, the above mentioned pharmaceutically active agents are preferably delivered when they are needed, i.e., at the onset of hyperplasia of smooth muscle cells. Otherwise, the agents may target other cells in the wall of a blood vessel and damage the blood vessel. To achieve a controlled, delayed delivery of the agents, one can use a stent having a polymeric coating prepared according to the method of this invention. Embedded in such a polymeric coating, the active agent close to the surface of the coating is released to a blood vessel shortly after implantation, while the active agent embedded more deeply need to diffuse slowly through the coating before reaching the surface. If a biodegradable polymer is included in the coating, the embedded active agent can be released rapidly after the initiation of polymer degradation. To achieve a desired delivery pattern, a coating can consist of both biodegradable and non-degradable polymers mixed at a suitable ratio.

The above-described coating may contain two adjacent layers made of the same material or different materials. Each layer may contain the same active agent or different agents. For example, a first agent disposed within a top biodegradable layer of the coating is released as the top layer degrades, and a second agent disposed within an inner non-degradable layer is released primarily by diffusion. As a result, one can achieve two distinct deliver patterns suitable for different agents. To prepare such a multi-layer coating, one sequentially coats a stent with different solutions containing different polymers and active agents by the method of the present invention.

An active agent can be mixed uniformly with a polymer in a solvent before coating onto a stent. The agent can also be encapsulated into nanospheres or microspheres using the method described in Ha JC. et al., J Control Release 1999 Dec 62:381–92. Suitable encapsulating polymers include poly(ethylene oxide) (PEO), poly(propyleneoxide) (PPO), or PEO-PPO-PEO based polymers. These nanospheres or microspheres not only stabilize active agents, but also produce a "burst release" of the agents, once the encapsulating polymeric walls are degraded.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

0.2 g PLLA, 0.2 g PCL (Polysciences, Inc., Warrington, Pa.), and 0.6 g curcumin (Sigma-Aldrich Chemicals) were dissolved in 20 ml of 1,4-dixoane. Using a transfer pipette, 0.2 to 0.5 ml of the resultant coating solution was dropped onto the exterior surface of an interstice-containing stent that was mounted on a thin stainless steel wire. The coating solution was allowed to migrate and evenly distributed along the stent and into the interstices. Two minutes later, the stent was rolled back and forth over a microscope slide glass surface. The excess coating solution spanning the interstices was dragged out of the stent due to the affinity between the glass and the solvent.

After the rolling process, the stent was dried in vacuum oven at 60° C. for 0.5 hour to remove residue solvent. The coated stent was then examined under a microscope. It was observed that the coating on the stent was bridge-free and conformal to the structure of the stent.

A coating was formed on another stent in the same manner described above except that a porous PVP sponge saturated with the coating solution was used as a substrate. The coating was also examined under a microscope and found to be bridge-free.

EXAMPLE 2

0.2 g of poly(ethylene acrylate) (Michelman Inc), 0.02 g of tirofiban, 0.2 g of curcumin, and 0.001 g of polyfunctional aziridine type crosslinker were dissolved in 20 ml of water to prepare a coating solution.

A stent was held by a robot arm and loosely mounted on the tip of a properly sized glass pipette. The other opening of the pipette was connected to a vacuum aspiration system. The diameter of the pipette was smaller than that of the lumen of the stent so that the pipette could be inserted through the lumen of the stent and freely moved with respect to the stent. The stent was so mounted that one of its ends was in proximity to the tip of the pipette. 0.2 to 0.5 ml of the coating solution described above was dropped onto the stent and allowed to migrate into the space between the interior surface of the stent and the exterior surface of the pipette. The vacuum aspiration pump connected to the pipette was turned on, and an air pressure difference thus generated removed the excess coating solution spanning the interstices of the stent that was in proximity to the tip the pipette.

The robot arm was then actuated to move the stent slowly toward to the tip of pipette at a speed of about 1 mm/sec. During the movement, the entire length of the stent passed by the tip and the excess coating solution spanning all interstices was aspirated away. After the coated stent was dislodged from the pipette, it was air-dried in a vacuum oven at 60° C. for 3 hours before being examined under a microscope. The coating was bridge-free and conformal to the structure of the stent.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of coating a polymer onto an implant having at least one interstice, the method comprising:

providing a solution containing a polymer;

applying the polymer-containing solution onto the implant;

contacting the outer surface of the implant with a surface of a substrate, so that any of the polymer-containing solution spanning the interstice is drawn to the surface of the substrate via affinity therebetween; and drying the polymer-containing solution to form a coating on the implant, wherein the contacting step is conducted by rolling the implant over the surface of the substrate.

2. The method of claim 1, wherein the implant is a stent or a coil.

3. The method of claim 2, wherein the surface of the substrate is flat.

4. The method of claim 2, wherein the surface of the substrate is concaved.

5. The method of claim 1, wherein the solution further contains a pharmaceutically active agent.

6. The method of claim 5, wherein the pharmaceutically active agent is curcumin.

7. The method of claim 1, wherein the polymer is biodegradable.

8. The method of claim 7, wherein the polymer is poly (L-lactic acid), polyglycolic acid, poly-lactic/polyglycolic acid co-polymer, poly(epsilon caprolactone), polyanhydrides, polyorthoesters, poly vinly acetate, polyhydroxybutyrate-polyhydroxyvalerate, and other aliphatic polyesters or collagen.

9. The method of claim 8, wherein the solution further contains curcumin.

10. The method of claim 1, wherein the polymer is non-biodegradable.

11. The method of claim 10, wherein the polymer is polyurethane, polyacrylates, polymethacrylates, polyethylene and polypropylene copolymers, epoxides, polyamides, polyesters or parylene.

12. The method of claim 11, wherein the solution further contains curcumin.

13. The method of claim 1, wherein the surface of the substrate is flat.

14. The method of claim 1, wherein the surface of the substrate is concaved.

15. The method of claim 1, wherein the substrate is made of glass, quartz, sponge, ceramic, stainless steel, paper, leather, or polymeric material.

* * * * *